United States Patent
von Hoffmann (10) Patent No.: US 6,461,347 B1
(45) Date of Patent: *Oct. 8, 2002

(54) LOW PROFILE CATHETER SHAFT

(75) Inventor: Gerard von Hoffmann, Trabuco Canyon, CA (US)

(73) Assignee: Progenix, LLC, Trabuco Canyon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,045

(22) Filed: Sep. 21, 1999

Related U.S. Application Data (60) Continuation of application No. 09/261,264, filed on Mar. 3, 1999, which is a division of application No. 08/813,822, filed on Mar. 6, 1997, now Pat. No. 5,879,324.

(51) Int. Cl.[7] .................. A61M 31/00; A61M 25/00; A61M 29/00
(52) U.S. Cl. .................. 604/508; 604/509; 604/510; 604/523; 606/194
(58) Field of Search .................. 604/506–510, 604/93.1, 96.01, 102.01–102.02, 103, 103.01, 103.04, 103.09, 104, 158, 164.13, 264, 523, 524, 528, 529, 532, 912, 915, 921; 606/192, 194

(56) References Cited

U.S. PATENT DOCUMENTS

| | | | |
|---|---|---|---|
| 4,406,656 A | * | 9/1983 | Hattler et al. |
| 4,496,347 A | | 1/1985 | MacLean et al. |
| 4,771,778 A | | 9/1988 | Mar |
| 4,773,901 A | | 9/1988 | Norton |
| 4,798,593 A | | 1/1989 | Iwatschenko |
| 4,808,164 A | | 2/1989 | Hess |
| 4,820,349 A | | 4/1989 | Saab |
| 4,824,435 A | | 4/1989 | Giesy et al. |
| 4,884,573 A | | 12/1989 | Wijay et al. |
| 5,047,045 A | | 9/1991 | Arney et al. |
| 5,053,004 A | | 10/1991 | Markel et al. |
| 5,203,338 A | | 4/1993 | Jang |
| 5,219,335 A | | 6/1993 | Willard et al. |
| 5,242,396 A | | 9/1993 | Evard |
| 5,254,090 A | | 10/1993 | Lombardi et al. |
| 5,255,668 A | | 10/1993 | Umeda |
| 5,290,247 A | | 3/1994 | Crittenden |
| 5,306,247 A | | 4/1994 | Pfenninger |
| 5,318,532 A | | 6/1994 | Frassica |
| 5,364,357 A | | 11/1994 | Aase |
| 5,369,755 A | | 11/1994 | Bodicky |
| 5,370,615 A | | 12/1994 | Johnson |
| 5,411,477 A | | 5/1995 | Saab |
| 5,464,398 A | | 11/1995 | Haindl |
| 5,470,322 A | | 11/1995 | Horzewski et al. |
| 5,472,418 A | | 12/1995 | Palestrant |
| 5,474,537 A | | 12/1995 | Solar |
| 5,480,383 A | | 1/1996 | Bagaoisan et al. |
| 5,484,408 A | | 1/1996 | Burns |
| 5,498,249 A | | 3/1996 | Quinn |
| 5,499,973 A | | 3/1996 | Saab |
| 5,533,968 A | | 7/1996 | Muni et al. |
| 5,540,798 A | | 7/1996 | DeMaio et al. |

(List continued on next page.)

Primary Examiner—Brian L. Casler
Assistant Examiner—Catherine Serke
(74) Attorney, Agent, or Firm—Knobbe, Martens, Olson & Bear, LLP (57) ABSTRACT

Disclosed is a low profile catheter shaft configuration for incorporation into any of a variety of catheters. The shaft comprises first and second side-by-side lumens with a movable wall extending axially therebetween. The first lumen may occupy more than half of the inside diameter of the shaft such as during advancement along a guidewire, and the second lumen may occupy more than half of the inside diameter such as following withdrawal of the guidewire and during inflation of a balloon. Methods are also disclosed.

58 Claims, 3 Drawing Sheets

U.S. PATENT DOCUMENTS

| | | |
|---|---|---|
| 5,549,552 A | 8/1996 | Peters et al. |
| 5,569,195 A | 10/1996 | Saab |
| 5,569,201 A | 10/1996 | Burns |
| 5,578,010 A | 11/1996 | Ashby |
| 5,587,125 A | 12/1996 | Roychowdhury |
| 5,591,129 A | 1/1997 | Shoup et al. |
| 5,599,325 A | 2/1997 | Ju et al. |
| 5,601,539 A | 2/1997 | Corso, Jr. |
| 5,728,067 A | 3/1998 | Enger |
| 5,807,311 A * | 9/1998 | Palestrant |
| 5,879,324 A * | 3/1999 | von Hoffmann ............ 604/49 |
| 6,007,517 A | 12/1999 | Anderson |

* cited by examiner

LOW PROFILE CATHETER SHAFT

This application is a continuation of Ser. No. 09/261,264, filed Mar. 3, 1999, which is a divisional of Ser. No. 08/813,822, filed Mar. 6, 1997, now U.S. Pat. No. 5,879,324.

BACKGROUND OF THE INVENTION

The present invention relates to catheters for percutaneous transluminal use. More particularly, the present invention relates to low profile catheter shaft designs for use with catheters intended for accessing remote or tortuous vascular locations.

A wide variety of interventional procedures have been developed which require access to remote parts of the vascular system. One increasingly utilized coronary revascularization procedure, for example, is percutaneous transluminal coronary angioplasty (PTCA). In a typical PTCA procedure, a guiding catheter having a prebent distal tip is percutaneously introduced at a remote location such as the femoral artery using a conventional Seldinger technique. The guide catheter is advanced retrograde until it reaches the ascending aorta with the distal tip seated in the ostium of a desired coronary artery. Steering is accomplished during transluminal advancement by torquing the proximal end of the guide catheter as needed until the distal tip is positioned in the ostium.

An elongate, flexible guidewire is then advanced through and out the distal end of the guide catheter, and negotiated through the tortuous vasculature of the coronary arteries until it crosses a lesion to be dilated. A dilatation catheter is thereafter advanced along the guidewire until the dilatation balloon is positioned within the lesion.

Once properly positioned, the balloon is inflated one or more times to an inflation pressure on the order of six to twelve atmospheres or higher to dilate the lesion. Balloon catheters sized for the coronary arteries may inflate to a diameter in the range of from about two to about four cm. Following dilatation, the balloon is deflated and the catheter is proximally withdrawn from the patient.

Considerable effort has been devoted to reducing the profile and improving the trackability (flexibility) of PTCA and other interventional catheters. Improvements of this nature can enable the catheter to reach more remote and smaller treatment sites. These capabilities can permit treatment of both more remote coronary arteries as well as other narrow and tortuous vessels such as within the intracranial vasculature.

A further requirement of a successful dilatation or other therapeutic or diagnostic catheter is that the catheter shaft exhibit sufficient pushability. Pushability relates to the longitudinal transmission of force along the axial length of the catheter from the proximal end to the distal end. This characteristic is necessary to enable the physician to advance the catheter against resistive forces such as due to the tortuous path and small diameter of the vessel and target stenosis.

Notwithstanding the significant research effort in this technology, there remains a need for a catheter shaft design which minimizes the crossing profile and yet retains sufficient columns strength and torquability for the intended clinical objective. Preferably, the catheter shaft design can be adapted for any of a variety of functional applications, such as balloon dilatation and or drug or stint delivery catheters, either in an over the wire or a rapid exchange configuration.

SUMMARY OF THE INVENTION

There is provided in accordance with one aspect of the present invention a low profile balloon catheter. The catheter comprises an elongate flexible tubular body, having a proximal section and a distal section. An inner collapsible tubular wall is provided in the distal section, for defining a guidewire lumen. An outer tubular wall concentrically disposed about the inner tubular wall defines a potential inflation lumen in between the inner tubular wall and the outer tubular wall. An inflatable balloon is provided on the distal section, in fluid communication with the inflation lumen.

In one embodiment, the catheter further comprises a transition between the proximal section and the distal section. The transition is at least about 3 cm from the distal end of the catheter.

In accordance with another aspect of the present invention, there is provided a method of performing a medical procedure on a patient. The method comprises the steps of providing a catheter having a distal section in which a first lumen is defined within a first collapsible tube, the first tube positioned within a second outer tube, and a second lumen is defined in a space between the first tube and the second tube. The guidewire is advanced through the patient to a site for performing the medical procedure. The catheter is advanced along the guidewire to the site, with the guidewire extending through the first lumen, wherein the first tube, second tube and guidewire are dimensioned such that when the guidewire is positioned within the first tube, the first tube substantially fills the second tube.

The catheter is positioned within the patient to perform the medical procedure at the site, and the guidewire is thereafter proximally withdrawn from at least the distal section of the catheter. At least a distal portion of the first tube is permitted to collapse, thereby increasing the available cross-sectional area of the second lumen. Media is thereafter introduced through the second lumen to treat the site.

In one embodiment, the catheter further comprises an inflatable balloon in fluid communication with the second lumen, and the introducing media step comprises introducing inflation media through the second lumen to inflate the balloon. In another embodiment, the catheter further comprises a plurality of drug delivery ports along the length of the catheter shaft, and the introducing media step comprises introducing drug through the second lumen to deliver the drug to the site.

In a further embodiment, the catheter comprises a transition between the proximal section and the distal section, and the withdrawing the guidewire step comprises withdrawing the distal end of the guidewire to a position between the distal end of the transition and the proximal end of the catheter. Preferably, the withdrawing the guidewire step comprises withdrawing the distal end of the guidewire to a point within the range of from about 3 cm to about 35 cm from the distal end of the catheter.

In accordance with a further aspect of the present invention, there is provided a method of dilating a stenosis in a vessel. The method comprises the steps of providing a balloon dilatation catheter having a distal tubular shaft section with an axially extending, laterally movable wall separating a first side of the movable wall from a second side of the movable wall. The catheter is axially slidably mounted on a guidewire, and percutaneously introduced and transluminally advanced along the guidewire such that the guidewire is on the first side of the movable wall.

The balloon is positioned at the stenosis, and the guidewire is withdrawn from the distal tubular shaft section. Inflation media is introduced through the catheter and along the second side of the movable wall to inflate the balloon. A first lumen in the distal section on the first side of the movable wall has a relatively greater cross-sectional area than a second lumen on the second side of the movable wall during the positioning step, and the second lumen has a relatively greater cross-sectional area than the first lumen during the introducing inflation media step.

In accordance with a further aspect of the present invention, there is provided a method of treating a patient. The method comprises the steps of providing a catheter having a guidewire lumen and at least a second lumen extending therethrough. A distal end of a guidewire is positioned in a patient, and the catheter is advanced over the guidewire and into the patient. The distal end of the guidewire is retracted to a position within the catheter, and media is thereafter introduced through the second lumen to treat the patient.

In one embodiment, the cross-sectional area of a portion of the second lumen is enlargeable following the retracting the distal end of the guidewire step. The introducing media step may comprise introducing inflation media for inflating a balloon, or introducing medication through the second lumen.

In accordance with a further aspect of the present invention, there is provided a method of dilating a stenosis in a body lumen. The method comprises the steps of providing a balloon dilatation catheter having at least a guidewire lumen and an inflation lumen extending therethrough. The balloon is positioned in the body lumen to dilate the stenosis, and a distal portion of the guidewire lumen is collapsed by introducing inflation media through the inflation lumen.

Further features and advantages of the present invention will become apparent from the detailed description of preferred embodiments which follows, when considered with the attached drawings and claims.

DETAILED DESCRIPTION OF PREFERRED EMBODIMENTS

Figure 1:
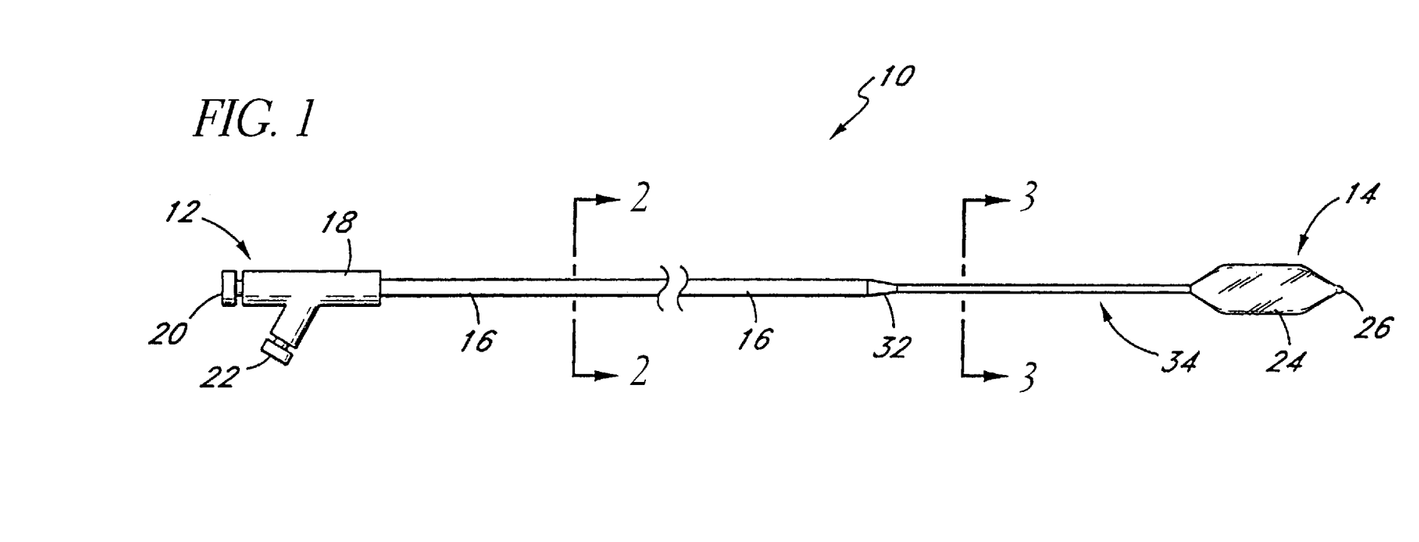
FIG. 1 is a side elevational view of an over the wire embodiment of a balloon dilatation catheter incorporating the catheter shaft of the present invention.

Referring to FIG. 1, there is disclosed a catheter 10 in accordance with one aspect of the present invention. Although described in the context of a balloon dilatation catheter, catheters incorporating the low profile shaft of the present invention can alternatively or additionally incorporate temporary stent, perfusion, drug delivery, stent placement or stent sizing features, or any combination of these features, as will be readily apparent to one of skill in the art in view of the disclosure herein.

The catheter 10 generally comprises an elongate tubular body 16 extending between a proximal end 12 and a distal functional end 14. The length of the tubular body 16 depends upon the desired application. For example, lengths in the area of about 120 cm to about 140 cm are typical for use in percutaneous transluminal coronary angioplasty applications. Intracranial applications may call for a different catheter shaft length depending upon the vascular access site, as will be apparent to those of skill in the art.

In the illustrated embodiment, the tubular body 16 is divided into at least a proximal section 33 and a distal section 34 separated by a transition 32, discussed infra. Alternatively, the collapsible inner tube within an outer tube construction of distal section 34 can extend the entire length of the catheter from the manifold 18 to distal tip 25, as will become apparent from the disclosure herein.

The proximal section 33 of tubular body 16 may be produced in accordance with any of a variety of known techniques for manufacturing balloon-tipped catheter bodies, such as by extrusion of appropriate biocompatible polymeric materials. Known materials for this application include high density polyethylene, polytetrafluoroethylene, nylons, and a variety of others such as those disclosed in U.S. Pat. No. 5,499,973 to Saab, the disclosure of which is incorporated in its entirety herein by reference. Alternatively, at least a proximal portion or all of the length of tubular body 16 may comprise a spring coil, solid walled hypodermic needle tubing, or braided reinforced wall, as is understood in the catheter and guidewire arts.

For most applications, the proximal section 33 of tubular body 16 is provided with an approximately circular cross-sectional configuration having an external diameter within the range of from about 0.025 inches to about 0.065 inches. In accordance with one embodiment of the invention, the proximal section 33 of tubular body 16 has an external diameter of about 0.042 inches (3.2 f) throughout most of its length. Alternatively, a generally oval or triangular cross-sectional configuration can also be used, as well as other noncircular configurations, depending upon the method of manufacture, number and arrangement of internal lumens and the intended use.

In a catheter intended for peripheral vascular applications, the proximal section 33 of body 16 will typically have an outside diameter within the range of from about 0.039 inches to about 0.065 inches. In coronary vascular applications, the proximal section 33 of body 16 will typically have an outside diameter within the range of from about 0.025 inches to about 0.045 inches. The illustrated construction of distal section 34 permits lower external cross-sections, as low as 0.028 inches or 0.025 inches or 0.022 inches or lower as may be desired for remote coronary or intracranial applications. Low diameter shafts in accordance with the present invention may also be dimensioned for use in ureters, Fallopian tubes and other lumens and potential lumens, as well.

Diameters outside of the preferred ranges may also be used, provided that the functional consequences of the diameter are acceptable for the intended purpose of the catheter. For example, the lower limit of the diameter for any portion of tubular body 16 in a given application will be a function of the number of fluid or other functional lumen contained in the catheter, together with the acceptable maximum flow rate of dilatation fluid or drugs to be delivered through the catheter, and the desired structural integrity.

Tubular body 16 must have sufficient structural integrity (e.g., column strength or "pushability") to permit the catheter to be advanced to distal locations without buckling or undesirable bending of the tubular body. The ability of the body 16 to transmit torque may also be desirable, such as to avoid kinking upon rotation and in embodiments having a drug delivery capability on less than the entire circumference of the delivery balloon. Larger diameters generally have sufficient internal flow properties and structural integrity, but reduce perfusion in the artery in which the catheter is placed. Increased diameter catheter bodies also tend to exhibit reduced flexibility, which can be disadvantageous in applications requiring advancement of the distal end of the catheter through highly tortuous pathways. In addition, lesions requiring treatment are sometimes located in particularly small diameter arteries, necessitating the lowest possible profile.

The proximal end 12 of catheter 10 is provided with a manifold 18 having one or more access ports as is known in the art. Generally, manifold 18 is provided with a guidewire port 20 in an over-the-wire embodiment and a balloon inflation port 22. Additional access ports are provided as needed, depending upon the functional capabilities of the catheter. Manifold 18 may be injection molded from medical grade plastics or formed in accordance with other techniques known in the art.

The distal end 14 of the illustrated catheter 10 is provided with an inflatable balloon 24, shown schematically in FIG. 1. However, in embodiments intended solely for nonballoon applications such as access catheters or nonballoon infusion, drug or embolic delivery catheters, the balloon 24 may be omitted.

The distal end 14 of the catheter 10 is further provided with an atraumatic distal tip 25 usually having a guidewire exit port 26 as is known in the art. Preferably, a radiopaque marker (not illustrated) is provided on the catheter body 16 to facilitate positioning of the catheter as is known in the art. Suitable marker bands can be produced from a variety of materials, including platinum, gold, and tungsten/rhenium alloy.

The distal tip 25 may be axially separated from the balloon 24 by a distal introduction segment having an outside diameter within the range of from about 0.014 inches to about 0.030 inches, and a length within the range of from about 2 mm to about 5 mm. In one embodiment, the introduction segment has an outside diameter of about 0.020 inches, and a length of about 2.0 mm.

Figure 2:
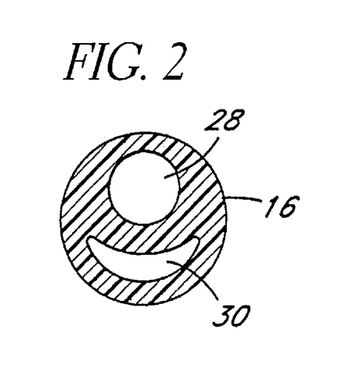
FIG. 2 is a cross-sectional view taken along the line 2—2 in FIG. 1.

Referring to FIG. 2, there is illustrated a cross-sectional view through the proximal section 33 of the catheter shaft 16. In the illustrated embodiment, the proximal section 33 comprises an extrusion, having a guidewire lumen 28 and an inflation lumen 30 as is known in the art. Alternatively, the proximal section 33 can be formed having a concentric configuration if desired.

In many applications, the proximal section 33 will not be required to traverse particularly low profile or tortious arteries. For example, in a typical PTCA application, the proximal section 33 will extend from a position outside of the patient distally through the guide catheter. Outside diameters of the proximal section 33 within the range of from about 0.03 inches to about 0.06 inches are generally suitable for this application. For this reason, any of a variety of known catheter shaft constructions, such as polymeric extrusions and hypotubes can be utilized for the proximal section 33.

In the illustrated embodiment, the proximal section 33 is separated from a distal section 34 by a transition 32. In the illustrated design, the side-by-side lumen configuration of the proximal section 33 converts in the transition 32 to a coaxial lumen orientation in the distal section 34. However, the catheter can readily be constructed utilizing a concentric or coaxial configuration throughout its entire length in view of the disclosure herein.

Figure 3A:
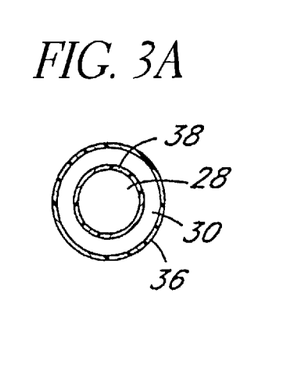
FIG. 3A is a cross-sectional view taken along the line 3—3 in FIG. 1 schematically illustrating a coaxial distal dual lumen configuration.
Figure 3B:
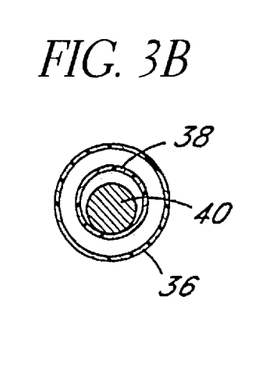
FIG. 3B is a cross-sectional view as in FIG. 3A, illustrating a guidewire in the central lumen.
Figure 3C:
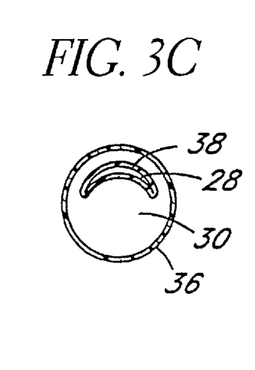
FIG. 3C is a cross-sectional view as in FIG. 3B, with the wall of the central lumen collapsed following proximal withdrawal of the guidewire to maximize the cross-sectional area of the outer lumen.

Referring to FIGS. 3A–3C, there is illustrated the collapsible interior wall feature of the present invention which permits a minimal outside diameter of the catheter shaft 16 at least in the distal section 34. Referring to FIG. 3A, an interior tubular wall 38 defines a central lumen 28. Central lumen 28 is referred to herein as the guidewire lumen, however, the central lumen 28 can be alternatively utilized for inflation media, drug delivery or other communication depending upon the catheter design.

The inner tubular wall 38 defining guidewire lumen 28 is positioned within an outer tubular wall 36. The outer wall 36 is illustrated as though it is spaced radially outwardly apart from the inner wall 38 to define an annular space 30 therebetween. Annular space 30 in the illustrated embodiment is utilized as an inflation lumen for inflating the balloon 24. However, as will become apparent in view of the disclosure herein, the inner wall 38 when in its enlarged interior cross-sectional area configuration may completely or substantially fill the area within outer wall 36. In this manner, the shaft OD can be minimized by reducing the inflation lumen 30 to a potential lumen when the inner wall 38 is filled by the guidewire. Following positioning of the balloon at a treatment site, and proximal withdrawal of the guidewire from at least a distal portion of inner wall 38, that portion of wall 38 can collapse to produce an inflation lumen without affecting the OD of the catheter shaft.

Referring to FIG. 3B, a guidewire 40 is illustrated as positioned within the guidewire lumen 28 defined by inner tubular wall 38. As can be appreciated by those of skill in the art, the diameter of the guidewire 40 is illustrated as slightly smaller (e.g., by about 0.001–0.003 inches) than the inside diameter of the tubular wall 38. Avoiding a tight fit between the guidewire 40 and inside diameter of guidewire lumen 28 enhances the slideability of the catheter over the guidewire. In ultra small diameter catheter designs, it may be desirable to coat the outside surface of the guidewire 40 and/or the inside surface of the inner tubular wall 38 with a lubricous coating to minimize friction as the catheter 10 is axially moved with respect to the guidewire 40. A variety of coatings may be utilized, such as Paralene, Teflon, silicone rubber, polyimide-polytetrafluoroethylene composite materials or others known in the art and suitable depending upon the material of the guidewire or inner tubular wall 38.

Figure 6:
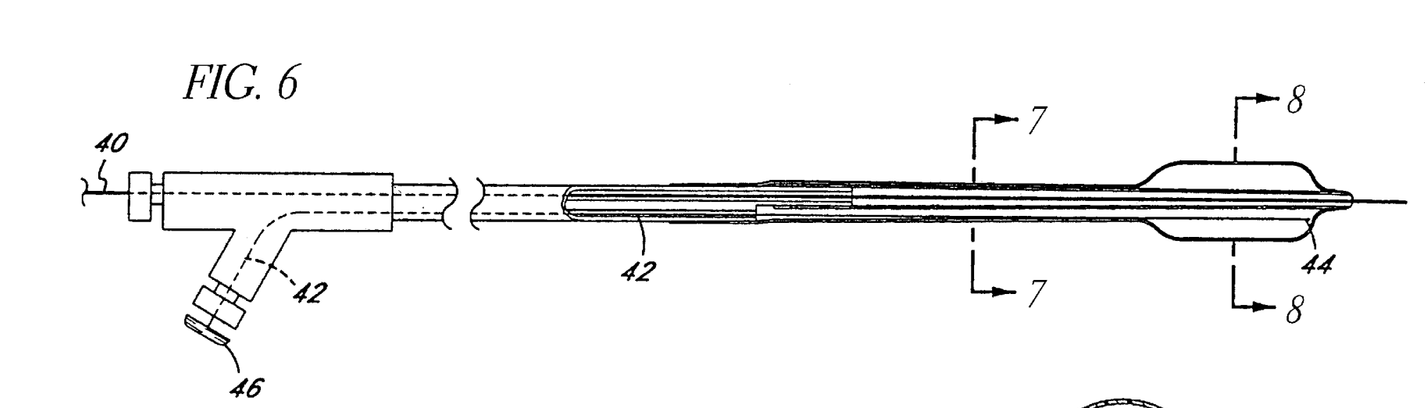
FIG. 6 is a partial cross-sectional, side elevational view of a catheter like that of FIG. 1, with a column strength support removably positioned in the inflation lumen.
Figure 7:
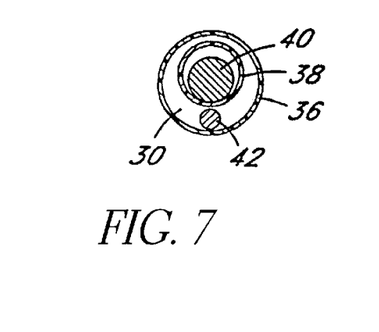
FIG. 7 is a cross-sectional view taken along the line 7—7 in FIG. 6.
Figure 8:
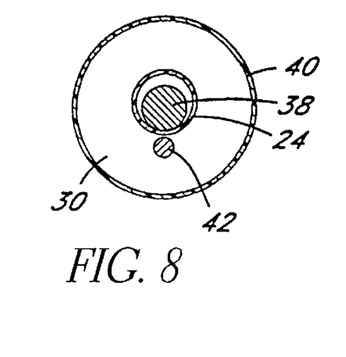
FIG. 8 is cross-sectional view taken along the line 8—8 in FIG. 6.

In FIGS. 3A and 3B, the inner tubular wall 38 is illustrated in an open, enlarged cross-sectional area configuration. In the open configuration, the outside diameter of inner tubular wall 38 may substantially fill the inside diameter of outer tubular wall 36. Alternatively, the inner tubular wall 38 may be spaced radially inwardly from the outer tubular wall 36 as illustrated. Some available cross-sectional area for lumen 30 even in the collapsed configuration is desirable in embodiments such as illustrated in FIGS. 6–8, so that a column support can fit in the inflation lumen during catheter placement.

Referring to 3C, the inner tubular wall 38 is illustrated in a collapsed, minimized interior cross-sectional area orientation following removal of guidewire 40. The effect of collapsing the inner tubular wall 38 as illustrated is to enlarge the available cross-sectional area of the second lumen 30 without the need to change the OD of the distal catheter section 34. The inner tubular wall 38 may collapse under its own bias, such as by providing the wall 38 with a preset during the catheter fabrication process. Alternatively, elastic materials can be utilized to retract the inner tubular wall 38 to a reduced cross-sectional area when not filled with the guidewire or pressurized media. As a further alternative, the inner tubular wall 38 is constructed from a flexible very thin material so that the inner tubular wall 38 collapses in response to introduction of inflation media or other material into second lumen 30.

The catheter shaft of the present invention can be constructed in any of several basic configurations. Selection of a particular one will depend primarily upon the length of the catheter which is expected to traverse a particularly low diameter or tortuous pathway.

For coronary vascular applications, for example, the proximal section 33 will be mostly or entirely within the relatively large diameter guide catheter. The transition 32 can be located on the catheter shaft 16 to correspond approximately with the distal end of the guide catheter when the balloon 14 is at the treatment site. Viewed the other way, the length of the distal section 34 is preferably at least as long as the distance from the ostium of the relevant coronary artery to the treatment site. In most applications, the transition 32 will be at least about 3 cm, preferably at least about 5 cm and alternatively as much as about 10 cm or 20 cm from the distal end of the catheter. Distances as much as 30 cm to 50 cm or greater between the transition 32 and distal end of the catheter may also be desirable in some applications.

For certain other applications, such as intracranial catheterizations, the distal section is preferably at least about 5 cm long and small enough in diameter to pass through vessels as low as 3 mm or lower. Catheters for this application may have a proximal section length of between about 60 cm to about 150 cm and a distal section length of between about 5 cm to about 15 cm, and the distal section is able to track a tortuous path of at least about 5 cm through vessels of less than about 3 cm lumen ID. Further dimensional and method disclosure can be found in U.S. Pat. No. 4,739,768, the disclosure of which is incorporated in its entirety herein by reference.

As an alternative to the illustrated embodiment, the tube-within-a-tube configuration can be utilized throughout the length of the catheter shaft, from the proximal manifold through the balloon. In this embodiment, the outer tube may comprise an extrusion using materials such as those disclosed previously herein, and a wall thickness sufficient to provide a reasonable degree of pushability. For example, a HDPE tube having an OD within the range of from about 0.024 inches to about 0.032 inches may have a wall thickness of about 0.003 inches. This "pushable" coaxial outer tube embodiment can alternatively have dissimilar proximal and distal sections such as a proximal hypotube section and a distal extrusion. A highly flexible, thin walled inner tube 38 extends throughout the length of the catheter in this embodiment. Wall thicknesses on the order of 0.001 inches or less are preferred, to minimize catheter profile and ensure collapsibility such as following proximal withdrawal of the guidewire to optimize the cross-sectional area of the inflation lumen.

Alternatively, very thin walled tubing can be used for the outer tube in either the distal section or throughout the length of the catheter, in addition to a very thin walled inner tube 38. In this construction, the catheter may not have sufficient pushability to reach the treatment site without the column support discussed in connection with FIGS. 6–8, infra.

Coaxial multilumen catheters known in the art generally are not available having a cross-section of much less than about 0.030 inches. Use of the configuration illustrated in FIGS. 1–3C, however, can permit a catheter to have an outside diameter in at least its distal section 34 of as low as about 0.006 inches or 0.008 inches greater than the diameter of the guidewire 40. In general, this is accomplished by the flexible wall of the present invention, which permits greater than 50% of the interior cross-sectional area to be used for the guidewire, and then, by withdrawal of the guidewire, greater than 50% of the interior cross-sectional area to be used for the inflation lumen.

For many conventional PTCA procedures, guidewires having an outside diameter in the range of from about 0.009 inches to about 0.015 inches are used. When used with a conventional 0.010 inch guidewire, for example, the catheter 10 of the present invention can be constructed utilizing an inner tube 38 having a wall thickness of about 0.001 inches, an inside diameter of about 0.012 inches, and an outside diameter of about 0.014 inches. In a minimum outside diameter embodiment, the outer tubular wall 36 may have an inside diameter of about 0.014 inches, and a wall thickness sufficient for the particular construction material to provide adequate pushability for the catheter. For many applications, this may be accomplished having an outer wall 36 thickness within the range of from about 0.002 inches to about 0.006 inches.

Thus, in the foregoing example, a wall thickness of about 0.003 inches will produce a catheter shaft with an OD of about 0.020 inches. When the guidewire extends through the inner tube 38, the ID of the inner tube is from 0.010 to 0.012 inches. Following withdrawal of the guidewire and introduction of inflation media into second lumen 30, the inner tube 38 will collapse to leave a second lumen 30 with a cross-sectional area roughly equivalent to that of a 0.010 inch–0.012 inch diameter lumen without any expansion of the OD of the catheter shaft.

Figure 4:
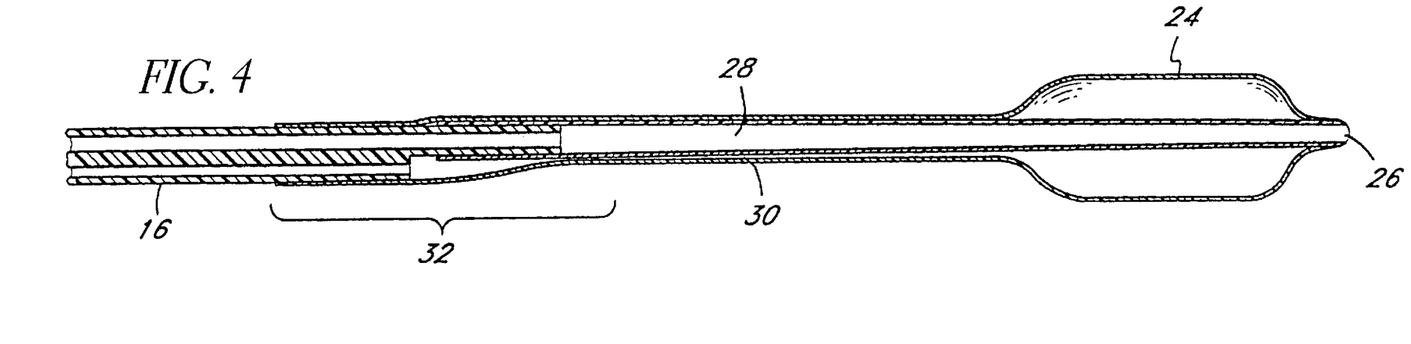
FIG. 4 is a side elevational, cross-sectional view of the distal portion of the catheter of FIG. 1.
Figure 5:
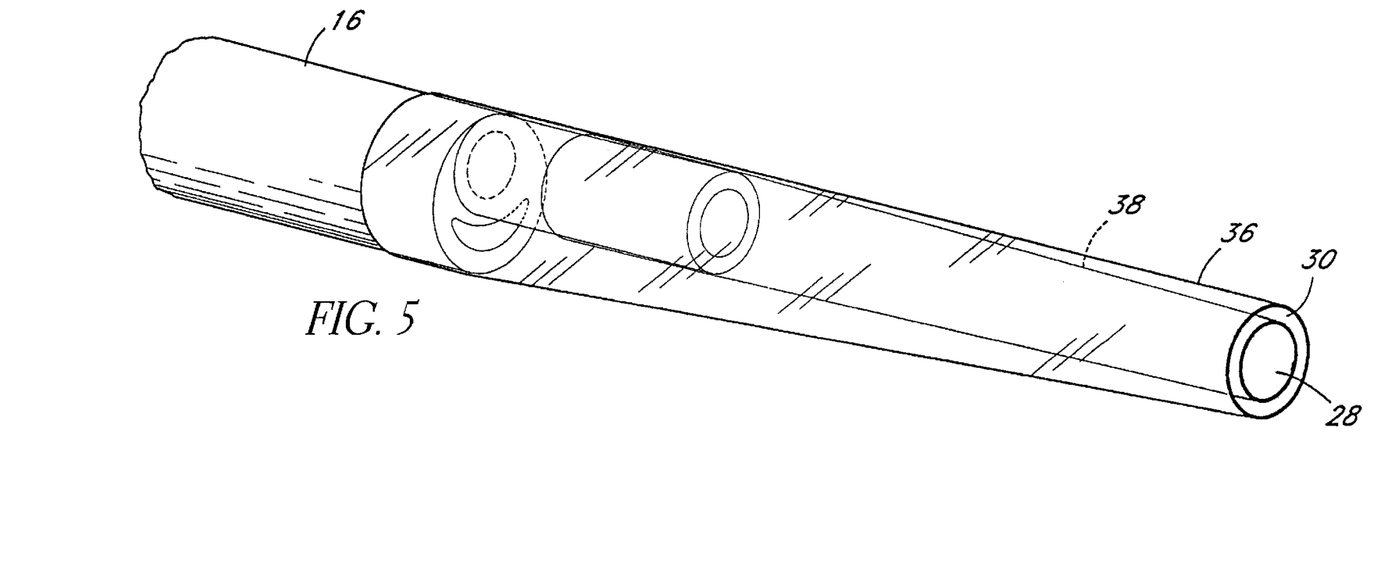
FIG. 5 is a schematic, perspective view of the transition zone 32 shown in FIG. 4.

Referring to FIGS. 4 and 5, there is illustrated a transition section 32 configuration in accordance with one aspect of the present invention. Transition 32 is useful in a catheter which incorporates the collapsible wall of the present invention only in a distal section 34 of the catheter. The proximal section 33 of shaft 16 comprises a guidewire lumen 28 and inflation lumen 30 in side-by-side orientation. The material of the extrusion can be cut away or otherwise formed to provide a stepped distal section. In this manner, a distal end 29 of the proximal section 33 containing guidewire lumen 28 is spaced distally in an axial direction from the distal end 31 of the portion of proximal section 33 containing inflation lumen 30.

Inner tubular wall 38 may comprise any of a variety of materials and dimensions, depending upon the intended application of the catheter. In one PTCA application, the inner wall 38 comprises a preformed PET tube having a wall thickness of about 0.001 inches. A proximal end of the PET tube is advanced coaxially over the distal end 29 of the proximal section 33, and is sealed to the distal end 29, such as by heat shrinking, adhesives, or through other techniques known in the art. An intermediate adhesion layer, surface treatment, or other steps may need to be taken to assure adhesion between the tube 38 and the material of the proximal extrusion 33, as will be appreciated by those of skill in the art depending upon the materials utilized. Suitable materials and techniques can be adapted from U.S. Pat. No. 5,569,201 to Burns and U.S. Pat. No. 5,587,125 to Roychowdhury, the disclosures of which are incorporated in their entirety herein by reference.

The outer tube 36 may then be advanced coaxially over the inner tube 38, and advanced proximally over the distal end 31 of proximal section 33. The outer tube 36 may similarly be attached to the proximal shaft section 33 such as by heat shrinking, adhesives, or other bonding techniques known in the art.

In the illustrated embodiment, the outer sleeve 36 is integrally formed with the balloon 24 thereon. From a manufacturing standpoint, this may be accomplished by forming the balloon 24 from tube stock as is known in the art, but with an extended proximal neck to form the tube 36. The distal end of the balloon 24 is provided with a distal neck portion 25 as is known in the art, which may be heat sealed or otherwise bonded to the inner tube 38 as will be appreciated by those of skill in the art.

Alternatively, the outer tube 36 may comprise an extrusion, particularly in an embodiment where additional column strength is desirable and/or minimizing crossing profile or outside diameter of the catheter is not critical. The balloon 24 may be separately formed and secured to the outside of the distal end of the extruded tubular body 36 as is well understood in the art. The extruded tubular body 36 may be provided with one or more apertures in a sidewall thereof, to permit communication between the second lumen 30 and the interior of the balloon 24.

In the embodiment illustrated in FIG. 4, the catheter can be constructed with a particularly low profile in the distal section 34. In addition, the crossing profile of the deflated balloon 24 can be very small. As a consequence, the pushability of the distal section 34 may not be sufficient for crossing tortious pathways or small diameter vessels. This is particularly so if the coaxial tube construction extends the entire length of the catheter 10.

Referring to FIG. 6, there is illustrated a pushability enhanced catheter in accordance with a further aspect of the present invention. In this embodiment, the basic catheter structure is the same as that illustrated in FIGS. 1–5. However, a removable column strength support 42 is positioned within the inflation lumen 30 to enhance the column strength of the catheter during the introduction step. The column strength support 42 generally comprises an elongate flexible wire, having a diameter within the range of from about 0.004 inches to about 0.016 inches, and preferably on the order of no more than about 0.012 inches. A rectangular ribbon can also be used, having an equivalent cross-sectional area.

The proximal end of the column support 42 is provided with a grip 46 such as a plastic cap which is molded or otherwise secured to the proximal end 43 of column support 42. Preferably, the plastic cap 46 is removably secured to the manifold 18 so that proximal advancement of the manifold causes a precisely commensurate proximal advancement of the column support 42. Removable attachment may be accomplished by using any of a wide variety of clips, twist fasteners such as luer connectors, interlocking snapfit connectors, friction fit connectors such as an OD toleranced to fit snugly within an ID on the manifold and the like as will be appreciated by those of skill in the art in view of the disclosure herein.

The axial length of column support 42 is preferably precisely calibrated to match the particular catheter 10 for which is be used. The distal end 44 of column support 42 is preferably positioned within a distal portion of the (collapsed) balloon 24, such as at the point of catheter manufacture. In this manner, the catheter is supplied to the clinical site with the column support 42 in place. The cap 46 is left connected to the manifold 18 during the catheter introduction and positioning step, to enhance the column strength of the distal section 34 of the catheter 10. Following placement of the balloon 24 across the site to be treated, the proximal cap 46 may be twisted, uncoupled, or otherwise disconnected from the manifold 18. Cap 46 and column support 42 may thereafter be proximally withdrawn from the catheter 10, and discarded. The inflation lumen 30 is thereafter fully available for transmission of inflation media.

The risk of puncture of column support 42 through the distal end of the balloon 24 can be minimized, such as providing a slightly enlarged atraumatic tip on distal end 44 of column support 42. In addition, the distal seal between the balloon 24 and the catheter shaft may be reinforced, such as through the use of a heat shrink reinforcing band for surrounding the catheter shaft adjacent distal tip 25, adhesives, or through other techniques that will be apparent to those of skill in the art in view of the disclosure herein. A column support anchor 46 can alternatively be secured to the inner tubular wall 38, such as a small, proximally facing anchor surface formed by an annular band or in the seal between tube 38 and the distal neck of balloon 24.

Thus, the present aspect of the invention provides a catheter which has a first, enhanced column strength for introduction and placement, and a second, reduced column strength for during the diagnostic or therapeutic step (e.g., balloon dilatation or drug delivery). The catheter also has a lumen for inflating the balloon or delivering medication which has a first, relatively small available cross-sectional area for during the catheter placement step, and a second, enlarged cross-sectional area for use following placement to inflate the balloon or infuse medication. The catheter thus has increased column strength for the placement step, and increased secondary lumen capacity for post placement use. This is accomplished by sacrificing column strength post placement when it is not needed, and by sacrificing secondary lumen capacity during placement, when it is not needed.

The catheter 10 may be provided with perfusion capabilities if desired in view of the intended use. A proximal perfusion zone can be formed proximally of the balloon 24 for carrying one or more proximal perfusion ports (not illustrated). The length and diameter of the perfusion zone can be varied depending upon desired flexibility and perfusion characteristics. In general, an outside diameter within the range of from about 0.02 inches to about 0.04 inches and a length of from about 5 mm to about 10 mm can be used. In one embodiment, the diameter is about 0.033 inches and the length is about 6.5 mm.

The number, size and position of the perfusion ports can be varied widely within the scope of the invention. In general, from about 2 to about 40 ports may be workable. Preferably, from about 6 to about 30 ports, each having a diameter of from about 0.014 inches to about 0.021 inches, are used.

The proximal perfusion ports are placed in fluid communication with one or more distal perfusion ports by way of a central lumen extending axially through the interior of the balloon 24. The distal perfusion ports extend through the wall of the catheter on the distal side of the balloon, and can have the same characteristics described in connection with the proximal perfusion ports.

The basic operation of a catheter such as that illustrated in FIG. 1 is as follows. In general, the guidewire will be positioned within the patient for directing the catheter to a treatment site. The catheter is loaded onto to the proximal end of the guidewire and advanced distally along the guidewire until the balloon 24 is positioned at the treatment site. During the positioning step, the cross-section in FIG. 3B most accurately represents the catheter configuration.

Following positioning of the balloon 24 at the treatment site, the guidewire 40 may be proximally withdrawn from the distal section 34 of the catheter. Preferably, the guidewire 40 is proximally withdrawn until the distal end (not illustrated) of the guidewire 40 is located in the transition 32 or in the proximal section 33.

In this manner, the central lumen 28 in the distal section 34 is no longer occupied by the guidewire, so the inner tube 38 can collapse as has been discussed to maximize the cross-sectional area of the second lumen 30 (see FIG. 3C). Inflation media can then be introduced through the second lumen 30 to inflate the balloon 24 and treat the site.

Following dilatation of the site, the inflation media can be withdrawn to deflate the balloon to facilitate removal of the catheter. Prior to removal (or repositioning) of the catheter, the guidewire is preferably advanced distally through central lumen 28 and out of the distal opening 26 so that it can remain across the treatment site. The catheter may thereafter be withdrawn, and a second catheter may be introduced along the same guidewire.

Thus, the present invention provides a catheter shaft configuration in which two or more interior lumen each have a variable cross-sectional area. For catheter placement along a guidewire, a first lumen has a first cross-sectional area to receive the guidewire and a second lumen has a third, reduced cross-sectional area. Following placement of the catheter and at least partial proximal withdrawal of the guidewire, the first lumen is reducible for a second, smaller cross-sectional area, thereby allowing the second lumen to be enlargeable to a fourth, enlarged cross-sectional area. In the context of a balloon catheter having two lumens, more than 50% of the first interior lumen cross-sectional area can be available for the guidewire, and then more than 50% of the total interior lumen cross-sectional area can be available for the inflation media, without enlarging the OD of the catheter and without using the same lumen for the guidewire and the inflation media.

Preferably, the catheter 10 is supplied in a kit with a guidewire which has been uniquely calibrated to the axial location of the transition 32 or other stopping point for the distal end of the guidewire. The guidewire is provided with a colored marker band or other indicium so that when the indicium appears as the guidewire is withdrawn proximally from the manifold 18, the clinician will know that the distal end of the guidewire has been withdrawn from the distal section 34. In an embodiment where the collapsible inner tube 38 extends the entire length of the catheter 10, it may be necessary to withdraw the guidewire all the way to the manifold 18 or from the catheter entirely to accommodate the inflation media in lumen 30.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

What is claimed is:

1. A method of treating a patient, comprising the steps of:
providing a catheter having a proximal end and a distal end, a guidewire lumen and at least a second lumen extending therethrough, the catheter having a first outside diameter proximal to a transition and a second, smaller outside diameter distal to the transition, the transition positioned in between the proximal end and the distal end;
positioning a distal end of a guidewire in the patient;
advancing the catheter over the guidewire and into the patient;
retracting the distal end of the guidewire to a position within the catheter at least as far as the transition;
retaining both the guidewire lumen and the second lumen patent proximally of the transition;
collapsing the guidewire lumen distally of the transition and opening the second lumen distally of the transition while maintaining the second diameter distal to the transition; and
treating the patient through the second lumen.

2. A method as in claim 1, wherein the transition is positioned within the range of from about 2 cm to about 50 cm from the distal end.

3. A method as in claim 1, wherein the transition is at least about 10 cm from the distal end.

4. A method as in claim 1, wherein the transition is positioned within the range of from about 3 cm to about 35 cm from the distal end.

5. A method as in claim 1, wherein the cross-sectional area of a portion of the second lumen is enlargeable following retracting the guidewire.

6. A method as in claim 1, wherein the position is within the distal one half of the axial length of the catheter.

7. A method as in claim 1, wherein the introducing media step comprises introducing inflation media for inflating a balloon.

8. A method as in claim 1, wherein the introducing media step comprises introducing medication through the second lumen.

9. A method as in claim 1, further comprising the step of inflating a balloon on the catheter.

10. A method as in claim 1, wherein the advancing a catheter step comprises advancing an over the wire catheter.

11. A method as in claim 1, wherein the advancing a catheter step comprises advancing a rapid exchange catheter.

12. A method of treating a patient, comprising the steps of:
providing a catheter having a proximal end and a distal end, a guidewire lumen, at least a second lumen extending therethrough, and an inflatable balloon thereon, the catheter having a first outside diameter proximal to a transition and a second, smaller outside diameter distal to the transition, the transition positioned in between the proximal end and the distal end;
positioning a distal end of a guidewire in the patient;
advancing the catheter over the guidewire and into the patient;
retracting the distal end of the guidewire to a position within the catheter at least as far as the transition;
retaining both the guidewire lumen and the second lumen patent proximally of the transition;
collapsing the guidewire lumen distally of the transition and opening the second lumen distally of the transition; and
introducing inflation media through the second lumen to inflate the balloon.

13. A method as in claim 12, wherein the transition is positioned within the range of from about 2 cm to about 50 cm from the distal end.

14. A method as in claim 12, wherein the transition is at least about 10 cm from the distal end.

15. A method as in claim 12, wherein the transition is positioned within the range of from about 3 cm to about 35 cm from the distal end.

16. A method as in claim 12, wherein the cross-sectional area of a portion of the second lumen is enlargeable following retracting the guidewire.

17. A method as in claim 12, wherein the position is within the distal one half of the axial length of the catheter.

18. A method as in claim 12, wherein the advancing a catheter step comprises advancing an over the wire catheter.

19. A method as in claim 12, wherein the advancing a catheter step comprises advancing a rapid exchange catheter.

20. A method of performing a treatment within a vascular lumen, comprising the steps of:
providing a catheter having a guidewire lumen and at least a second lumen extending side by side in at least a distal portion of the catheter, the guidewire lumen having an interior cross sectional area of A1 and the second lumen having an interior cross sectional area of A2 measured in the same transverse plane as the area A1;
advancing the catheter transluminally along a guidewire to a treatment site, while A1 is greater than 50% of the sum of A1+A2;
enlarging the cross sectional area of the second lumen such that A2 is greater than 50% of the sum of A1+A2, to permit treating the site; and
inflating a balloon on the catheter within the vessel.

21. A method of performing a treatment as in claim 20, further comprising the step of perfusing blood past the balloon while the balloon is inflated.

22. A method of performing a treatment as in claim 20, further comprising the step of introducing inflation media into the second lumen.

23. A method of performing a treatment as in claim 20, further comprising the step of introducing medication into the second lumen.

24. A method of performing a treatment as in claim 20, wherein the enlarging step comprises laterally moving an interior wall which separates the guidewire lumen from the second lumen.

25. A method of performing a treatment as in claim 24, wherein the distal section has an axial length within the range of from about 2 cm to about 50 cm.

26. A method of performing a treatment as in claim 25, wherein the distal section has an axial length within the range of from about 3 cm to about 35 cm.

27. A method of performing a treatment as in claim 20, further comprising the step of retracting a guidewire part way but not completely from the catheter prior to the enlarging step.

28. A method of performing a treatment as in claim 27, wherein the retracting step comprises retracting the guidewire until an indicium appears at the proximal end of the catheter.

29. A method of performing a treatment as in claim 28, wherein the indicium comprises a color change on the guidewire.

30. A method of treating a patient, comprising the steps of:
providing a rapid exchange catheter having a proximal end and a distal end, a guidewire lumen and at least a second lumen extending therethrough, the catheter having a first outside diameter proximal to a transition and a second, smaller outside diameter distal to the transition, the transition positioned in between the proximal end and the distal end;
positioning a distal end of a guidewire in the patient;
advancing the rapid exchange catheter along the guidewire and into the patient;
retracting the distal end of the guidewire to a position within the catheter at least as far as the transition;
retaining both the guidewire lumen and the second lumen patent proximally of the transition;
collapsing the guidewire lumen distally of the transition and opening the second lumen distally of the transition; and
introducing media through the second lumen to treat the patient.

31. A method as in claim 30, wherein the transition is positioned within the range of from about 2 cm to about 50 cm from the distal end.

32. A method as in claim 30, wherein the transition is at least about 10 cm from the distal end.

33. A method as in claim 30, wherein the transition is positioned within the range of from about 3 cm to about 35 cm from the distal end.

34. A method as in claim 30, wherein the cross-sectional area of a portion of the second lumen is enlargeable following retracting the guidewire.

35. A method as in claim 30, wherein the position is within the distal one half of the axial length of the catheter.

36. A method as in claim 30, wherein the introducing media step comprises introducing inflation media for inflating a balloon.

37. A method as in claim 30, wherein the introducing media step comprises introducing medication through the second lumen.

38. A method as in claim 30, further comprising the step of inflating a balloon on the catheter.

39. A method of performing a treatment within a vascular lumen, comprising the steps of:
providing a catheter having a guidewire lumen and at least a second lumen extending side by side in at least a distal portion of the catheter, the guidewire lumen having an interior cross sectional area of A1 and the second lumen having an interior cross sectional area of A2 measured in the same transverse plane as the area A1;
advancing the catheter transluminally along a guidewire to a treatment site, while A1 is greater than 50% of the sum of A1+A2; and
enlarging the cross sectional area of the second lumen such that A2 is greater than 50% of the sum of A1+A2, to permit treating the site;
wherein the enlarging step comprises laterally moving an interior wall which separates the guidewire lumen from the second lumen.

40. A method of performing a treatment as in claim 39, further comprising the step of inflating a balloon on the catheter within the vessel.

41. A method of performing a treatment as in claim 40, further comprising the step of perfusing blood past the balloon while the balloon is inflated.

42. A method of performing a treatment as in claim 39, further comprising the step of introducing inflation media into the second lumen.

43. A method of performing a treatment as in claim 39, further comprising the step of introducing medication into the second lumen.

44. A method of performing a treatment as in claim 39, wherein the distal section has an axial length within the range of from about 2 cm to about 50 cm.

45. A method of performing a treatment as in claim 44, wherein the distal section has an axial length within the range of from about 3 cm to about 35 cm.

46. A method of performing a treatment as in claim 39, further comprising the step of retracting a guidewire part way but not completely from the catheter prior to the enlarging step.

47. A method of performing a treatment as in claim 46, wherein the retracting step comprises retracting the guidewire until an indicium appears at the proximal end of the catheter.

48. A method of performing a treatment as in claim 47, wherein the indicium comprises a color change on the guidewire.

49. A method of performing a treatment within a vascular lumen, comprising the steps of:

providing a catheter having a guidewire lumen and at least a second lumen extending side by side in at least a distal portion of the catheter, the guidewire lumen having an interior cross sectional area of A1 and the second lumen having an interior cross sectional area of A2 measured in the same transverse plane as the area A1;

advancing the catheter transluminally along a guidewire to a treatment site, while A1 is greater than 50% of the sum of A1+A2;

enlarging the cross sectional area of the second lumen such that A2 is greater than 50% of the sum of A1+A2, to permit treating the site; and retracting a guidewire part way but not completely from the catheter prior to the enlarging step.

50. A method of performing a treatment as in claim 49, further comprising the step of inflating a balloon on the catheter within the vessel.

51. A method of performing a treatment as in claim 50, further comprising the step of perfusing blood past the balloon while the balloon is inflated.

52. A method of performing a treatment as in claim 49, further comprising the step of introducing inflation media into the second lumen.

53. A method of performing a treatment as in claim 49, further comprising the step of introducing medication into the second lumen.

54. A method of performing a treatment as in claim 49, wherein the enlarging step comprises laterally moving an interior wall which separates the guidewire lumen from the second lumen.

55. A method of performing a treatment as in claim 54, wherein the distal section has an axial length within the range of from about 2 cm to about 50 cm.

56. A method of performing a treatment as in claim 55, wherein the distal section has an axial length within the range of from about 3 cm to about 35 cm.

57. A method of performing a treatment as in claim 49, wherein the retracting step comprises retracting the guidewire until an indicium appears at the proximal end of the catheter.

58. A method of performing a treatment as in claim 57, wherein the indicium comprises a color change on the guidewire.

* * * * *